US010393636B2

(12) United States Patent
Pawliszyn et al.

(10) Patent No.: US 10,393,636 B2
(45) Date of Patent: Aug. 27, 2019

(54) SYSTEM AND METHOD FOR DESORBING AND DETECTING AN ANALYTE SORBED ON A SOLID PHASE MICROEXTRACTION DEVICE

(71) Applicants: Janusz Pawliszyn, Waterloo (CA); Marcos Tascon, Berazategui (AR); Varoon Singh, Nallasopara West (IN)

(72) Inventors: Janusz Pawliszyn, Waterloo (CA); Marcos Tascon, Berazategui (AR); Varoon Singh, Nallasopara West (IN)

(*) Notice: Subject to any disclaimer, the term of this patent is extended or adjusted under 35 U.S.C. 154(b) by 0 days.

(21) Appl. No.: 16/002,350

(22) Filed: Jun. 7, 2018

(65) Prior Publication Data
US 2019/0003936 A1 Jan. 3, 2019

Related U.S. Application Data

(63) Continuation of application No. 15/591,506, filed on May 10, 2017, now abandoned, and a continuation of
(Continued)

(51) Int. Cl.
*G01N 1/40* (2006.01)
*G01N 1/44* (2006.01)
(Continued)

(52) U.S. Cl.
CPC ....... *G01N 1/405* (2013.01); *A61B 5/150358* (2013.01); *G01N 1/44* (2013.01);
(Continued)

(58) Field of Classification Search
CPC .......... A61B 10/0045; A61B 5/150358; G01N 1/405; G01N 1/44; G01N 2001/1445;
(Continued)

(56) References Cited

U.S. PATENT DOCUMENTS 7,211,189 B2 * 5/2007 Jinno ................. B01J 20/28014
210/198.2
2003/0190757 A1 * 10/2003 Furuno .................. G01N 30/08
436/178
(Continued)

*Primary Examiner* — Jennifer Wecker

(57) ABSTRACT

Disclosed herein is a system for desorbing and detecting an analyte sorbed on a solid phase microextraction (SPME) device. This SPME device The system includes a desorption chamber containing solvent required for desorption of analytes from SPME device; a flow injector in fluid connection with the desorption chamber, the desorption chamber and the flow injector being fluidly connected by at least a flow-insulating fluid connector; a solvent source in fluid connection with the flow injector; and a fluid switch that: in a desorption position, allows the solvent to be sprayed from the flow injector while flow-insulating any desorption solution in the desorption chamber, and in an detecting position, turns off the solvent source while maintaining the fluid connection between the flow injector and the desorption chamber, transferring the desorption solution through the flow-insulating fluid connector to the flow injector as a substantially undiluted plug of liquid. The SPME device can be configured to be various morphologies such as, fibers, blades, thin film membranes and even magnetic particles. When magnetic particles are used an additional holder that contains an embedded magnet which holds a plate with a well to hold said magnetic particles is added to the system.

13 Claims, 16 Drawing Sheets

Related U.S. Application Data application No. PCT/CA2017/050562, filed on May 10, 2017.

(60) Provisional application No. 62/516,815, filed on Jun. 8, 2017.

(51) Int. Cl.
| | |
|---|---|
| *G01N 30/00* | (2006.01) |
| *G01N 21/71* | (2006.01) |
| *G01N 27/62* | (2006.01) |
| *G01N 30/06* | (2006.01) |
| *A61B 5/15* | (2006.01) |
| *H01J 49/16* | (2006.01) |
| *A61B 10/00* | (2006.01) |
| *G01N 1/14* | (2006.01) |
| *H01J 49/04* | (2006.01) |
| *G01N 30/72* | (2006.01) |

(52) U.S. Cl.
CPC .............. *G01N 30/00* (2013.01); *G01N 30/06* (2013.01); *H01J 49/165* (2013.01); *A61B 10/0045* (2013.01); *G01N 21/714* (2013.01); *G01N 27/622* (2013.01); *G01N 30/7266* (2013.01); *G01N 2001/1445* (2013.01); *G01N 2030/009* (2013.01); *G01N 2030/062* (2013.01); *G01N 2560/00* (2013.01); *H01J 49/0431* (2013.01); *Y10T 428/2933* (2015.01)

(58) Field of Classification Search
CPC ....... G01N 2030/009; G01N 2030/062; G01N 30/06; G01N 2560/00; H01J 49/165; Y10T 428/2933

See application file for complete search history.

(56) References Cited

U.S. PATENT DOCUMENTS

| | | | | |
|---|---|---|---|---|
| 2004/0241721 | A1* | 12/2004 | Gjerde | G01N 1/34 435/6.12 |
| 2005/0118599 | A1* | 6/2005 | Pawliszyn | A61B 10/0045 435/6.12 |
| 2005/0276727 | A1* | 12/2005 | Pawliszyn | A61B 5/14514 422/537 |
| 2015/0318160 | A1* | 11/2015 | Pawliszyn | H01J 49/0409 250/282 |

* cited by examiner

SYSTEM AND METHOD FOR DESORBING AND DETECTING AN ANALYTE SORBED ON A SOLID PHASE MICROEXTRACTION DEVICE

This application is a continuation of the U.S. Continuation-in-Part application Ser. No. 15/591,506, WIPO (PCT) Patent Application Number: PCT/CA2017050562 both filed on May 10, 2017. This application benefits from priority of U.S. Provisional Application No. 62516815.

BACKGROUND

Field

The present disclosure relates to systems and methods for desorbing and detecting an analyte sorbed on a solid phase microextraction device.

The following paragraph is not an admission that anything discussed in them is prior art or part of the knowledge of persons skilled in the art.

Solid phase microextraction (SPME) is a sampling technique that uses a sorbent-coated substrate to extract an analyte from a sampling media. In order to detect the analyte sorbed on the sorbent, the SPME device is transferred to the injection port of a separating and/or detecting instrument, such as a mass spectrometer. The analyte is desorbed from the sorbent coating of the SPME device and provided to the separating and/or detecting instrument.

INTRODUCTION

The following part is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

Desorption of an analyte sorbed on an SPME device into a detecting instrument is often performed under conditions of constant flow of a carrier stream. For example, desorption into an electrospray ionization-mass spectrometer (ESI-MS) may be performed by constantly flowing a solvent from a solvent source to an electrospray needle, nebulizing the solvent as it flows from the needle, and transferring the components of the nebulized solvent to the mass spectrometer. When an SPME device is placed in the solvent flow, the analyte is desorbed by the solvent and the desorbed analytes are transferred to the mass spectrometer for detection with help of the solvent. Similar techniques are used with other detecting instruments that use a flowing carrier stream to transfer analytes from the SPME device to the detecting instrument.

Some systems and methods that use a continuous flow of solvent to perform the desorption may generate broad extraction chronograms because, for example, the desorption is not instantaneous, some analytes may desorb at a slower rate than other analytes, or analytes may disperse during transport. For example, the SPME device may be positioned in an extraction chamber that inefficiently mixes the desorption solution. In such an extraction chamber, some of the desorbed analytes may be transported to the mass spectrometer in desorption solution that is sucked into solvent flowing past the extraction chamber, while other desorbed analytes may be further from the flowing solvent and must first diffuse through substantially stagnant desorption solution before being sucked into the flowing solvent.

Therefore, there remains a need for a method and system that transfer the desorption solution in a desorption chamber to a flow injector of a detecting instrument as a substantially undiluted plug of liquid.

SUMMARY OF THE INVENTION

In one aspect, the present disclosure provides a system for desorbing and detecting an analyte sorbed on a solid phase microextraction (SPME) device. The system includes a desorption chamber sized to accept the SPME device while defining a void volume of less than about 50 µL. The system also includes a flow injector in fluid connection with the desorption chamber. The desorption chamber and the flow injector are fluidly connected by at least a flow-insulating fluid connector. The system includes a solvent source in fluid connection with the flow injector, and a fluid switch. The fluid switch has a desorption position and a detecting position. In the desorption position, the fluid switch allows the solvent to be sprayed from the flow injector while flow-insulating any desorption solution in the desorption chamber. In the detecting position, the fluid switch isolates the solvent source from the flow injector by turning off the solvent flow while maintaining the fluid connection between the flow injector and the desorption chamber so as to transfer desorption solution in the desorption chamber through the flow-insulating fluid connector to the flow injector as a substantially undispersed plug of liquid.

In one particular example of a system according to the present disclosure, the flow-insulating fluid connector is dimensioned to reduce or avoid diffusion of desorption solution from the desorption chamber to the solvent flowing to the flow injector when (a) the fluid switch is in the desorption position, and (b) the solvent flows from the solvent source to the flow injector. For example: the flow-insulating fluid connector may have a smaller cross-section than a cross-section of the desorption chamber, and/or the flow-insulating flow connector may be sufficiently long in comparison to its cross-section that liquid flowing past one end of the fluid connector does not affect liquid at the other end of the fluid connector.

In another particular example of a system according to the present disclosure, the flow-insulating fluid connector may be sized to be fluidly blocked by an accepted SPME device, thereby fluidly isolating the desorption chamber from the flow injector during desorption. This configuration may be used to increase the duty cycle of the system by sequentially empting a plurality of desorption chambers connected to the same solvent flowing system by sequentially unblocking the flow-isolating fluid connector of each desorption chamber.

In another aspect, the present disclosure provides a method for desorbing and detecting an analyte sorbed on a solid phase microextraction (SPME) device. The method includes: desorbing at least some of the analyte from the SPME device into a desorption solution in a desorption chamber where the desorption solution in the desorption chamber is substantially not flowing to a flow injector. The method includes flushing substantially all of the desorption solution in the desorption chamber to the flow injector as a substantially undiluted plug of liquid. The desorption solution is sprayed by the flow injector into a detection device.

In one particular example of a method according to the present disclosure, the desorption chamber is in fluid connection with the flow injector, and the method includes nebulizing a solvent from the flow injector while the analyte is desorbing into the desorption solution in the desorption chamber. The solvent may be nebulized from the flow injector at a rate sufficient to fluidly isolate the desorption solution in the desorption chamber from the solvent being nebulized. The desorption solution in the desorption chamber may be flushed to the flow injector by (a) reducing the flow rate of solvent provided to the flow injector, or (b) fluidly isolating the flow injector from the solvent source, thereby hydrodynamically driving the desorption solution in the desorption chamber to the flow injector by suction generated by a nebulizing gas.

In another particular example of a method according to the present disclosure, the desorption chamber is not in fluid connection with the flow injector while the analyte is desorbing into the desorption solution in the desorption chamber. In such an example, flushing the desorption solution in the desorption chamber to the flow injector includes making a fluid connection between the desorption chamber and the flow injector. The SPME device may be used to break the fluid connection between the desorption chamber and the flow injector while the analyte is desorbing from the SPME device by blocking an aperture fluidly connected to the flow injector. In such a method, making the fluid connection between the desorption chamber and the flow injector may include unsealing the aperture by removing the SPME device. This method may additionally include sequentially empting a plurality of desorption chambers into to the same solvent flowing system by unblocking each the aperture fluidly connected to each flow injector to transfer the desorption solution to the flow injector. Such a method increases the duty cycle and throughput when the desorption of the analytes from the SPME device takes longer than the detection of the analytes.

Also, another embodiment related to the present disclosure is the dispositive for holding, containing and putting in contact magnetic particles (extractive material) with the insulated desorption flow. The embodiment also includes a polymeric well containing the magnetic particles. This device fits perfectly with the geometry of the flow injector allowing close contact between the surface of the magnetic particles and the solvent. In this step, the analytes of interest extracted by the extractive phase are transferred from the this phase to the desorption solvent. In the next step, and by means of the same mechanisms aforementioned, the plug of sample is transferred to the detection system.

BRIEF DESCRIPTION OF THE DRAWINGS

Embodiments of the present disclosure will now be described, by way of example only, with reference to the attached Figures.

DETAILED DESCRIPTION

Figure 1:
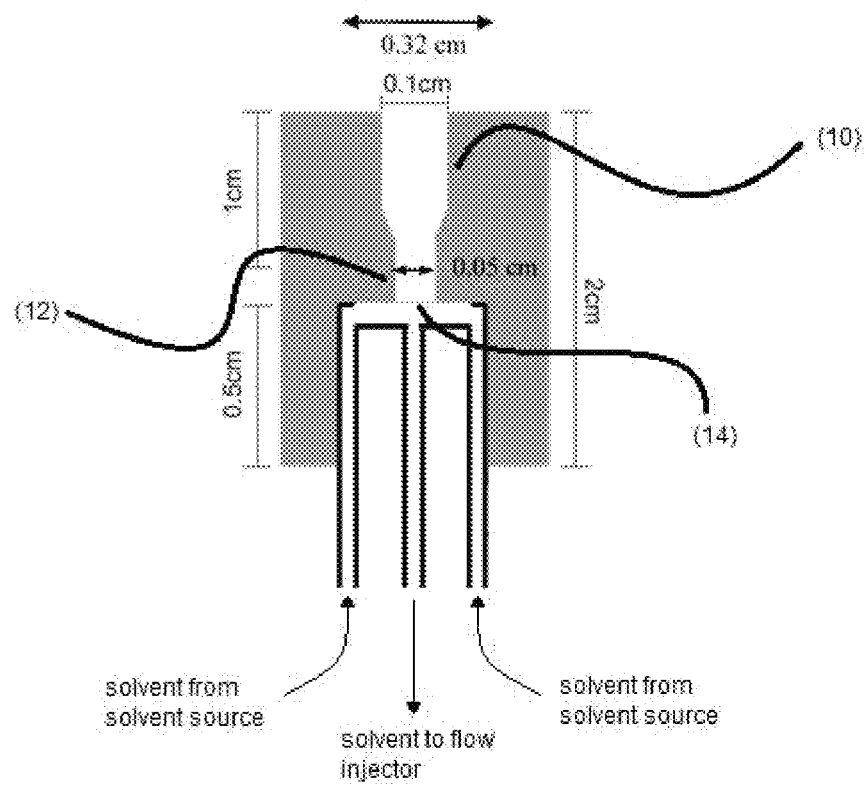
FIG. 1 is a cut-away side view of an exemplary desorption chamber and fluid-isolating flow connector according to the present disclosure.

Generally, the present disclosure provides a system and a method for desorbing and detecting an analyte sorbed on a solid phase microextraction (SPME) device. The system and method transfer the desorption solution in a desorption chamber to a flow injector of a detecting instrument as a substantially undiluted plug of liquid.

The system includes a desorption chamber sized to accept the SPME device while defining a void volume of less than about 50 µL.

The term "void volume" should be understood to refer to the volume available to the desorption solvent when the SPME device is in the desorption chamber. It is desirable to use as small a void volume as possible because smaller void volumes reach equilibrium faster than larger void volumes and, under non-equilibrium desorption times, reducing the void volume can produce for a given desorption time a desorption solution with a more concentrated analyte in comparison to larger void volumes. In some examples, the void volume may be a volume from about 3 to about 50 µL or any volume there between, such as 3 µL, 4 µL, 5 µL, 10 µL, 20 µL, 30 µL, 40 µL, or 50 µL.

SPME devices are substrates coated with a solid or liquid extraction phase, which may also be referred to as the "sorbent". The substrate may be, for example, a needle. Exemplary SPME devices are discussed in U.S. Pat. Nos. 7,232,689; 7,259,019; 7,384,794; 7,479,390; 8,008,064; 8,080,407; 8,114,660; and 8,598,325; and in U.S. Patent Publication Nos. US2015/0318158; and US2015/0318160.

The system also includes a flow injector in fluid connection with the desorption chamber. A flow injector would be understood to refer to an injector, such as a needle, that takes a liquid and injects it into a flowing transfer stream, such as a transfer gas. The transfer stream transports the analyte into the detecting instrument. Depending on the detecting instrument, the liquid may ionized and/or at least partially vaporized. In some examples, the flow injector may be a nebulizing needle. In other examples, the flow injector may be an electrospray needle.

The desorption chamber and the flow injector are fluidly connected by at least a flow-insulating fluid connector. The expressions "flow-insulating" should be understood to refer to a fluid connector that is sized and/or shaped to reduce or prevent fluid in the desorption chamber from mixing with fluids flowing in the rest of the system when the analyte is being desorbed from the SPME device. The fluid connector allows the solution in the desorption chamber to flow to the flow injector during the detection step, during which time the desorption solution may mix with fluids outside of the desorption chamber but is preferably transported to the flow injector with minimum mixing with fluids outside of the desorption chamber.

Insulating the desorption solution in the desorption chamber from fluids flowing in the rest of the system during the desorption step allows the concentration of the analyte in the desorption solution to increase over time, such as until an equilibrium concentration is reached. Insulating the desorption solution in the desorption chamber from fluids flowing in the rest of the system during the desorption step may also increase stability in the detection system. In void volumes of less than about 50 µL, where the desorption solution is flow-insulated from fluids in the rest of the system, the analyte may reach an equilibrium concentration in as little as 10 seconds. The time needed to reach equilibrium may be shorted by vibrating the SPME device in the desorption chamber and/or by heating the desorption solvent or the SPME device to increase mass transfer in the system. The terms "insulated" and "isolated" when used to discuss a fluid, solvent, or solution, are equivalent and should be understood to refer to reducing or preventing the fluid, solvent, or solution from mixing with other fluids in the system.

The system also includes a solvent source in fluid connection with the flow injector, and a fluid switch having at least a desorption position and a detecting position. In the desorption position, the fluid switch allows the solvent to be sprayed from the flow injector while flow-insulating any desorption solution in the desorption chamber. In the detecting position, the fluid switch isolates the solvent source from the flow injector by turning-off the solvent flow, while maintaining the fluid connection between the flow injector and the desorption chamber so as to transfer desorption solution in the desorption chamber through the flow-insulating fluid connector to the flow injector as a substantially undiluted plug of liquid.

In the context of the present disclosure, the expression "substantially undiluted plug of liquid" should be understood that at least 90% of the desorption solution in the desorption chamber is transferred to the flow injector in a single volume of fluid, and that the analyte concentration in the plug of fluid once it reaches the flow injector is at least 90% of the analyte concentration in the plug of fluid leaving the desorption chamber.

In one example of a system according to the present disclosure, the flow-insulating fluid connector is dimensioned to reduce or avoid diffusion of desorption solution from the desorption chamber to the solvent flowing to the flow injector when (a) the fluid switch is in the desorption position, and (b) the solvent flows from the solvent source to the flow injector. The flow-insulating fluid connector may have a sufficiently smaller cross-section than a cross-section of the desorption chamber; the length of the flow-insulating flow connector may be sufficiently greater than the cross-section of the flow flow-insulating connector that liquid flowing past one end of the fluid connector does not affect liquid at the other end of the fluid connector; or both. The expressions "sufficiently smaller cross-section" and "length of the flow-insulating flow connector may be sufficiently greater" should be understood to refer to fluid connectors that are dimensioned to prevent or reduce fluid at one of the fluid connector from interacting with fluid at the other end of the fluid connector. A fluid connector that is sufficiently small in cross-section and/or sufficiently long can reduce or prevent turbulent fluid flow at a first end of the connector from affecting the fluid at a second end of the connector, thereby fluidly isolating the fluid at the second end from fluid at the first end.

In another example of a system according to the present disclosure, the flow-insulating fluid connector is sized to be fluidly blocked by an accepted SPME device. Blocking the fluid connector fluidly isolates the desorption chamber from the flow injector during desorption. Such an exemplary system may also include at least one additional desorption chamber sized to accept an additional SPME device while defining a void volume of less than about 50 µL. The additional desorption chamber may be: connected in parallel to the first desorption chamber through an additional flow-insulating fluid connector that is sized to be fluidly blocked by an additional accepted SPME device. In this manner, this exemplary system can desorb analytes from a plurality of SPME devices, and can inject desorption fluid from one of the SPME devices while the other SPME device(s) are desorbing. A system that includes such a plurality of desorption chambers in parallel may allow the overall throughput to be increased, thereby increasing the duty cycle, even while the time for a single desorption and detection operation is unchanged.

In systems according to the present disclosure, the flow injector may be an electrospray needle, a thermospray nebulizer, a microelectrospray needle, an atmospheric pressure chemical ionization nebulizer, an ion-mobility spectrometry (IMS) nebulizer, an inductively coupled plasma (ICP) nebulizer, or any device that produces a pressure deferential that drives the flow towards the detecting instrument.

The detecting instrument in a system according to the present disclosure may be a mass spectrometer (such as IMS, electrochemical, or spectroscopy based detection) downstream of the flow injector for detecting the desorbed analyte.

Detecting instruments used in a system according to the present disclosure may be operated at a pressure lower than the desorption chamber, which may be at atmospheric pressure. During operation, the flow injector may generate a local low pressure, or the solvent source may have a pressure applied. In either situation, a pressure differential is generated that sucks solvent from the flow injector to the detecting instrument. When the fluid switch is in the desorption position, the solvent being sucked from the flow injector to the detecting instrument is the solvent in the desorption chamber.

A system according to the present disclosure may include a gas source for nebulizing solvent flowing from the flow injector. The gas may be an inert gas. A system may also include an agitator to vibrate an accepted SPME device, a heater to heat the desorption chamber, or both. Agitating the SPME device and heating the desorption fluid in the desorption chamber may increase the rate of analyte desorption.

In another aspect, the present disclosure provides a method for desorbing and detecting an analyte sorbed on a solid phase microextraction (SPME) device. The method includes desorbing at least some of the analyte from the SPME device into a desorption solution in a desorption chamber. The desorption solution in the desorption chamber is substantially not flowing to a flow injector during the desorption. The method includes flushing substantially all of the desorption solution in the desorption chamber to the flow injector as a substantially undiluted plug of liquid. The SPME device may be left in the desorption chamber, or may be removed from the desorption chamber. Removing the SPME device may more efficiently empty the desorption chamber. The method also includes spraying the desorption solution through the flow injector into a detection device. The expression "substantially not flowing to a flow injector" should be understood to mean that the desorption solution is fluidly isolated from fluid flowing to the flow injector.

The desorption chamber may be in fluid connection with the flow injector, and the method may include nebulizing a solvent from the flow injector while the analyte is desorbing into the desorption solution in the desorption chamber. The solvent may be nebulized from the flow injector at a rate sufficient to fluidly isolate the desorption solution in the desorption chamber from the solvent being nebulized. Nebulizing the solvent draws fluid from the flow injector. When there is a differential between the flow rate of fluid being drawn from the flow injector and the flow of fluid being provided to the system, fluid may be drawn from the desorption chamber (if the flow rate out of the flow injector is greater) or may be driven into the desorption chamber (if the flow rate into the system is greater) to fill-up the chamber for the next desorption. Further, the flow rate of fluid passing the desorption chamber may affect the mixing of fluid at the entrance of the desorption chamber. In some examples, a fluid velocity of at least about 0.4 cm/s passing by a flow-isolating connector having a sub-microliter volume fluidly isolates the desorption solvent in the desorption chamber. Accordingly, the rate of nebulizing the solvent affects fluid flow into and out of the desorption chamber when the desorption chamber is in fluid connection with the flow injector.

The desorption solution in the desorption chamber may be flushed to the flow injector by (a) reducing the flow rate of solvent provided to the flow injector, or (b) fluidly isolating the flow injector from the solvent source. In either case, the desorption solution in the desorption chamber is hydrodynamically driven to the flow injector by suction generated by the nebulizing gas. The desorption chamber may be refilled by (a) increasing the flow rate of solvent provided to the flow injector in comparison to the flow rate of solvent being nebulized, or (b) decreasing the flow rate of solvent being nebulized in comparison to the flow rate of solvent provided to the flow injector.

In another exemplary method, the desorption chamber is not in fluid connection with the flow injector while the analyte is desorbing into the desorption solution in the desorption chamber, and the method includes flushing the desorption solution in the desorption chamber to the flow injector by making a fluid connection between the desorption chamber and the flow injector. For example, the SPME device can be shaped to facilitate the break in the fluid connection between the desorption chamber and the flow injector while the analyte is desorbing from the SPME device by blocking an aperture fluidly connected to the flow injector. In such a situation, making the fluid connection between the desorption chamber and the flow injector may include unsealing the aperture sealed by the SPME device. The method may include removing the SPME device from the desorption chamber and inserting another SPME device into the desorption chamber to again block the aperture, for example once desorption solvent has been hydrodynamically driven into the desorption chamber. The method may include re-filling the desorption chamber with solvent supplied from the solvent source.

The method may be operated with a plurality of SPME devices being desorbed in parallel. For example, the method may include desorbing, flushing, and spraying an analyte from at least two SPME devices. The desorbed analytes from one of the SPME devices may be flushed to the flow injector and detected by the detecting instrument while the analytes from the other SPME devices are being desorbed in their respective desorption chambers.

The method may include heating the desorption chamber, vibrating the SPME device, or both. Doing so may increase the rate of analyte desorption. Under some conditions, the desorption may be effected for 5 to 20 seconds in order to desorb a sufficient amount of analyte to be detected. In some methods, such as methods that use relatively thicker coatings, the desorption is effected for more than 20 seconds.

Systems and methods according to the present disclosure may have an increased sensitivity, narrower chronogram bands, more reproducible desorption volumes, and/or more reproducible results over systems and methods with desorption chambers that are not fluidly isolated during desorption.

In a system where the desorption chamber is not fluidly isolated during desorption, analyte sorbed on one portion of the SPME coating may take a longer time to travel to the detector than analyte sorbed on another portion of the SPME coating. For example, some desorbed analyte may be transported to the detector by suction flow only, while other desorbed analyte may need to first travel by diffusion before reaching a part of the diffusion chamber where fluid is transported by suction flow to the detector. Since systems and methods according to the present disclosure transport the desorption solvent in substantially a single plug of fluid, the time difference to travel to the detector for analytes at the front of the plug of fluid vs. analytes at the back of the plug of fluid is based only on the volume of the desorption chamber and the flow rate.

Using a desorption chamber with known dimensions where the volume of desorption solvent does not vary over time (since the desorption chamber is fluidly isolated during desorption) may provide a more reproducible desorption volume, which may result in more reproducible desorption results.

Reducing the void volume of the desorption chamber reduces the dilution factor. Desorption chambers according to the present disclosure may have a volume of about 7 µL and a void volume of about 4 µL when the SPME fiber occupies 3 µL, while the total volume of a conventional open port probe (OPP) (i.e. volume of the gap and dome) over a 5 second desorption period is 30-40 µL.

One example of a desorption chamber and flow-insulating flow connector that may be used in a system according to the present disclosure is illustrated in FIG. 1. The desorption chamber (10) is fluidly connected to the flow injector (not illustrated) through the flow-insulating flow connector (12). Fluid travels as noted by the arrows from the solvent source, past the aperture (14) of the flow connecter (12) without significantly disturbing solvent in the desorption chamber (10), and to the flow injector. The dimensions of one specific example are shown in FIG. 1, but it should be understood that these are exemplary only and that the size and shape of the desorption chamber and/or fluid connector may be varied in view of the discussion above.

Figure 2:
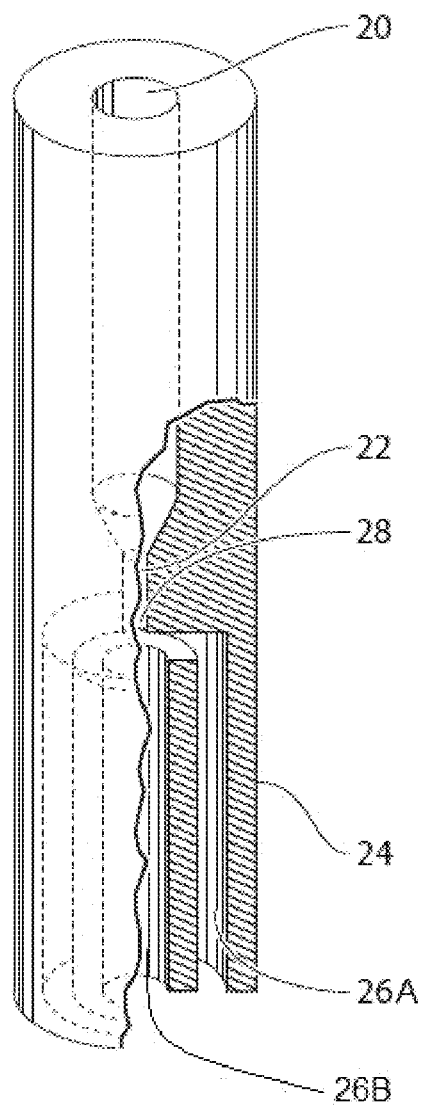
FIG. 2 is a three-quarter view of an exemplary desorption chamber and fluid-isolating flow connector according to the present disclosure.

Another example of a desorption chamber and flow-insulating flow connector that may be used in a system according to the present disclosure is illustrated in FIG. 2. The desorption chamber (20) is fluidly connected to the flow injector (not illustrated) through the flow-insulating flow connector (22). Fluid travels up base (24) through an inflow passage (26A) and past the aperture (28) of the flow connecter (22) without significantly disturbing solvent in the desorption chamber (20), and then down to the flow injector through an outflow passage (26B). The inflow passage (26A) and the outflow passage (26B) are fluidly connected and may be formed though the nesting of concentric cylinders, with the inflow passage (26A) defined by the space between the two cylinders and the outflow passage (26B) defined by the interior space of inner cylinder. The flow-insulating connector (22) illustrated in FIG. 2 has a volume of about 0.25 µL, and the desorption chamber (20) illustrated in FIG. 2 has a volume of about 7 µL.

Figure 3:
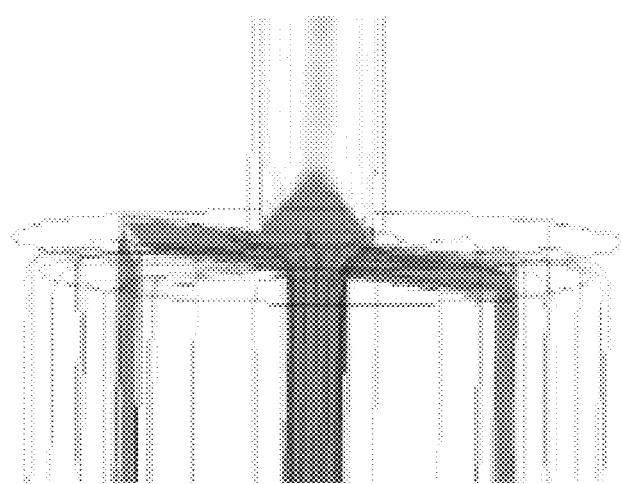
FIG. 3 is an illustration of flow rates in a slice of the fluid-isolating flow connector illustrated in FIG. 2.

The fluid velocity of solvent in the passages and the flow connector of FIG. 2 under steady state conditions is illustrated in FIG. 3 where darker colors represent faster fluid velocity and lighter colors represent slower fluid velocity. The flow profile calculated to generate FIG. 3 was based on a two-dimensional version of the embodiment illustrated in FIG. 2. The fluid velocity in the darkest portions of FIG. 3 represents a velocity of about 0.4 cm/s, while the fluid velocity in the lightest portions represents a velocity of about 0.05 cm/s. Regulating the suction conditions, such as generated by the Venturi effect at the flow injector, and the pump flow conditions allows the fluid flowing through the passages to reach an equilibrium state in which a constant rate of fluid is injected by the flow injector while, at the same time, a stagnant volume of fluid is achieved in the desorption chamber. This is evidenced by the flow lines and velocity gradients shown in FIG. 3 which shows that an SPME fiber can be placed in the desorption chamber without interfering in the electrospray process.

Figure 4:
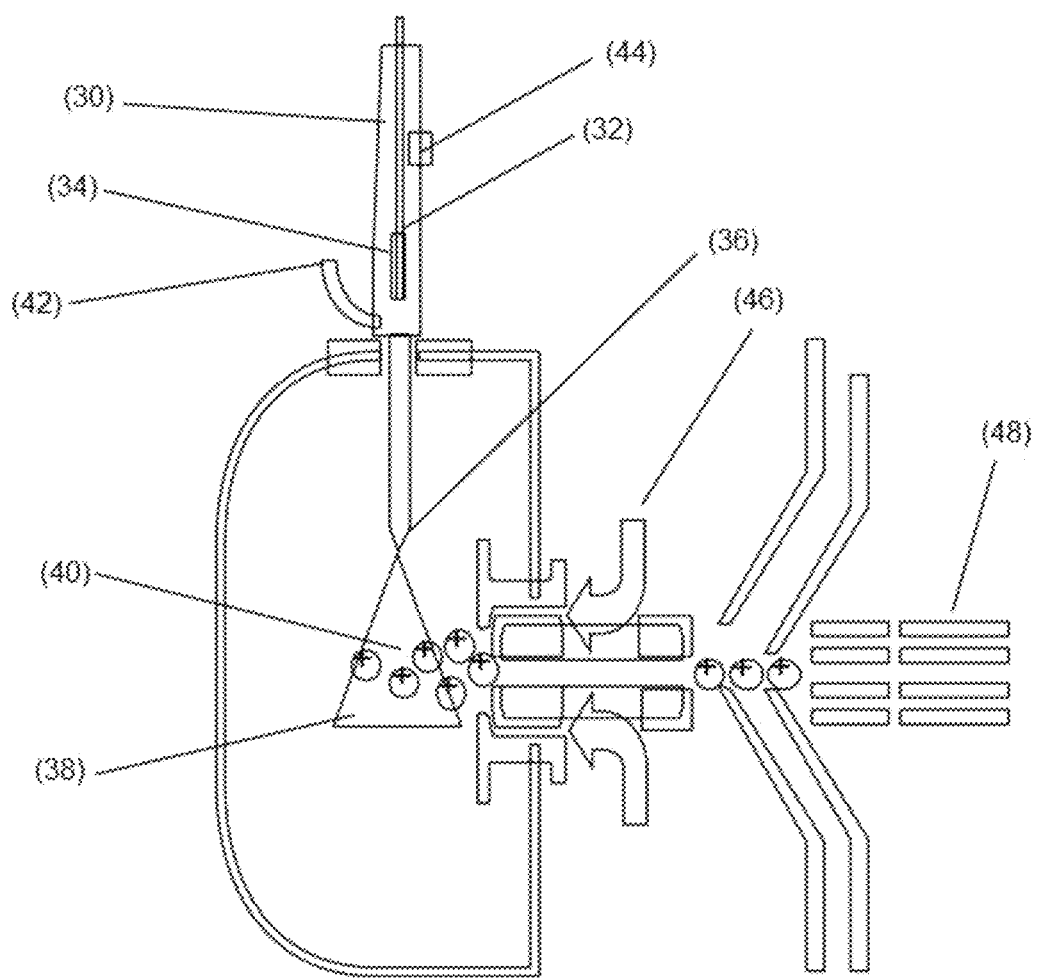
FIG. 4 is a schematic illustration of an exemplary system according to the present disclosure

A schematic illustration of a system according to the present disclosure is shown in FIG. 4. The desorption chamber (30) is illustrated as having an SPME fiber (32) inserted into the chamber. The SPME fiber has an extraction coating (34). The desorption chamber (30) is fluidly connected to an electrospray needle (36). The electrospray needle produces an electrospray cone (38) of charged components (40) from the solvent. The desorption chamber is also fluidly connected to a tube or passage (42) that can provide solvent to the desorption chamber by increasing the fluid flow rate from the tube (42) in comparison to the flow generated by the electrospray needle (36). The chamber also includes an optional fluid sensor (44) that may be used to automatically stop the filling of the desorption chamber. FIG. 4 also illustrates the flow of a drying gas (46) and a mass spectrometer (48) as a detector for the electrosprayed charged components (40).

Figure 5:
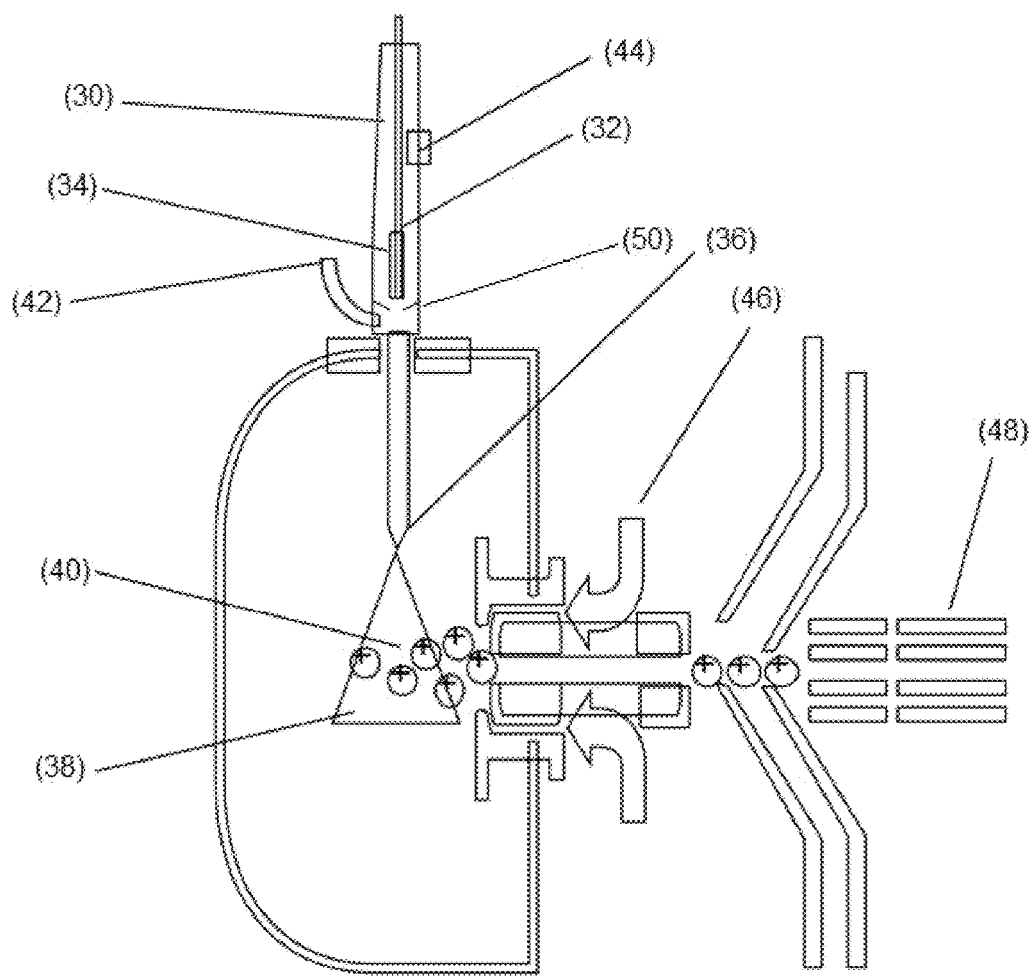
FIG. 5 is a schematic illustration of an exemplary system according to the present disclosure
Figure 6:
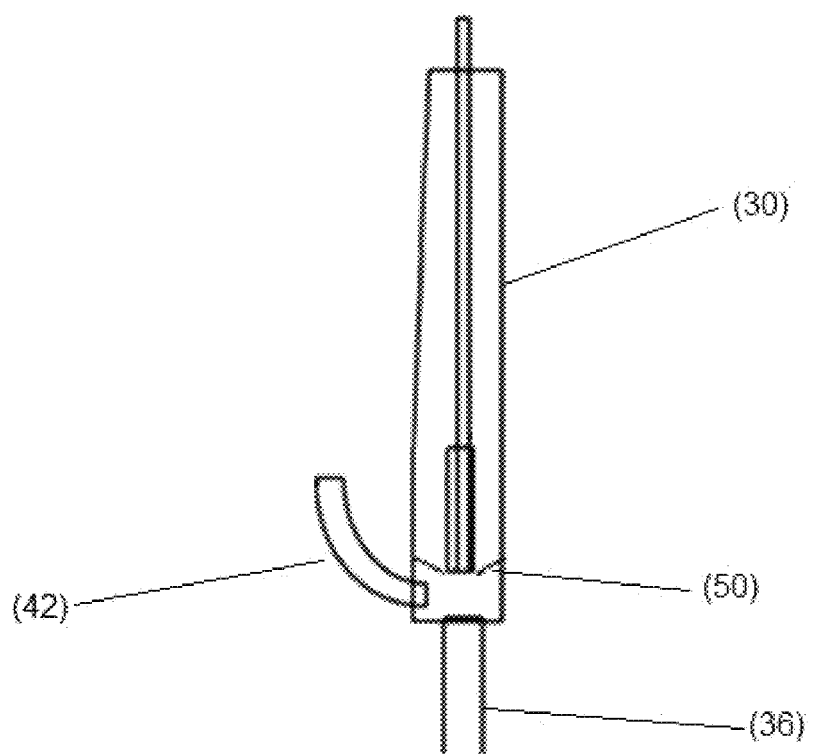
FIG. 6 is an illustration of an exemplary desorption chamber and fluid-isolating flow connector according to the present disclosure.

FIG. 5 shows a schematic illustration of a system similar to the system illustrated in FIG. 4 and, accordingly, the reference numerals are unchanged. However, the system of FIG. 5 additionally includes a narrowed orifice (50) that better fluidly isolates the desorption chamber (30) from the flow of fluid travelling to the electrospray needle (36). In some examples, the orifice (50) may be closed or blocked by the insertion of a SPME device, as illustrated in FIG. 6 which shows the desorption chamber (30), part of the electrospray needle (36), and the orifice (50). In this illustration, the SPME device is moved so that it blocks the orifice (50), thereby preventing or reducing a flow of desorption solvent into the electrospray needle (36) even while fluid flows through the tube or passage (42). Movement of the SPME device away from the orifice (50) opens the desorption chamber and desorption solution can flow to the electrospray needle. The flow of desorption solution to the electrospray needle may be increased by reducing or stopping the flow of fluid from the tube or passage (42).

EXAMPLE

LC-MS grade methanol (MeOH), acetonitrile (ACN), water and isopropanol (IPA) were provided by Fisher Scientific. Codeine, cocaine, buprenorphine, clenbuterol, sertraline, oxycodone and salbutamol were purchased from Sigma Aldrich (Oakville, ON, Canada). The fibers evaluated for extractions were manufactured using an in-house procedure. The coatings used were a mixture of HLB (hydrophilic-lipophilic balance) 5 µm particles and polyacrylonitrile (PAN) prepared by painting the SPME surface with a dispersion of HLB particles (10% by weight) in acrylonitrile monomer, followed by polymerization at 150° C. The fibers were coated having a coating thickness of 20 µm and a length of 4 mm. The experiments were carried out in a triple quadrupole API-4000 from SCIEX.

A desorption chamber as illustrated in FIG. 1 was used, and may be referred to as a modified open port probe (OPP). The desorption chamber was machined from Teflon for its chemical inertness. The desorption chamber includes a hole of 1 mm diameter and 1 cm length that has an approximate volume of 7 µL. The desorption chamber is connected to a flow restriction 0.5 mm in diameter, which generates an additional back pressure to the pump flow. The space between the fitting of the modified OPP and the desorption chamber was minimized (less than 1 mm) in order to reduce the dwell volumes. The system was connected to a 6-port valve in order to bypass the pump flow and produce an efficient flush of the chamber.

The ESI-MS flow conditions of the nebulizer gases (Nitrogen) in the modified open port probe (OPP) were: 90 PSI for gas 1, 70 PSI for gas 2, and 20 PSI for curtain gas 20 PSI. The electrospray voltage was 5500 V.

The MS/MS transitions monitored are shown in Table 1:

TABLE 1

MS/MS transitions and collision energies employed

| Compound | Precursor (m/z) | Product (m/z) | Collision Energy (V) |
| --- | --- | --- | --- |
| Oxycodone | 316.098 | 241.054 | 27 |
| Clenbuterol | 276.971 | 202.995 | 16 |
| Salbutamol | 240.071 | 148.071 | 18 |
| Codeine | 300.385 | 165.054 | 39 |
| Cocaine | 304.089 | 182.093 | 18 |
| Sertraline | 306.356 | 159.000 | 26 |
| Buprenorphine | 468.250 | 396.111 | 38 |

The modified OPP was tested using a standard solution of 50 ng/mL of each compound in phosphate buffer solution (PBS). The compounds were extracted using an SPME fiber from a 300 µL of sample for 10 minutes at 1500 rpm. The compounds were desorbed for 5 seconds by placing the SPME fiber in the desorption chamber. After this time, the SPME fiber was taken out from the chamber and the valve was switched to the flushing position for 3 seconds. In the flushing position, methanol from a solvent source is not traveling past the desorption chamber and is instead being actively pumped into the waste. In the flushing position, the only hydrodynamic driven force on the fluid in the desorption chamber is the Venturi suction due to the electrospray. In this manner, a plug of approximate 7 µL is directly injected in to the mass spectrometer with no further dilution. The desorption chamber is refilled by decreasing the Venturi suction for 3 seconds, which can be achieved by reducing the gas 1 pressure from 90 to 80 PSI and switching the valve to the desorption position. Finally, the chamber was ready to use for further experiments.

Figure 7:
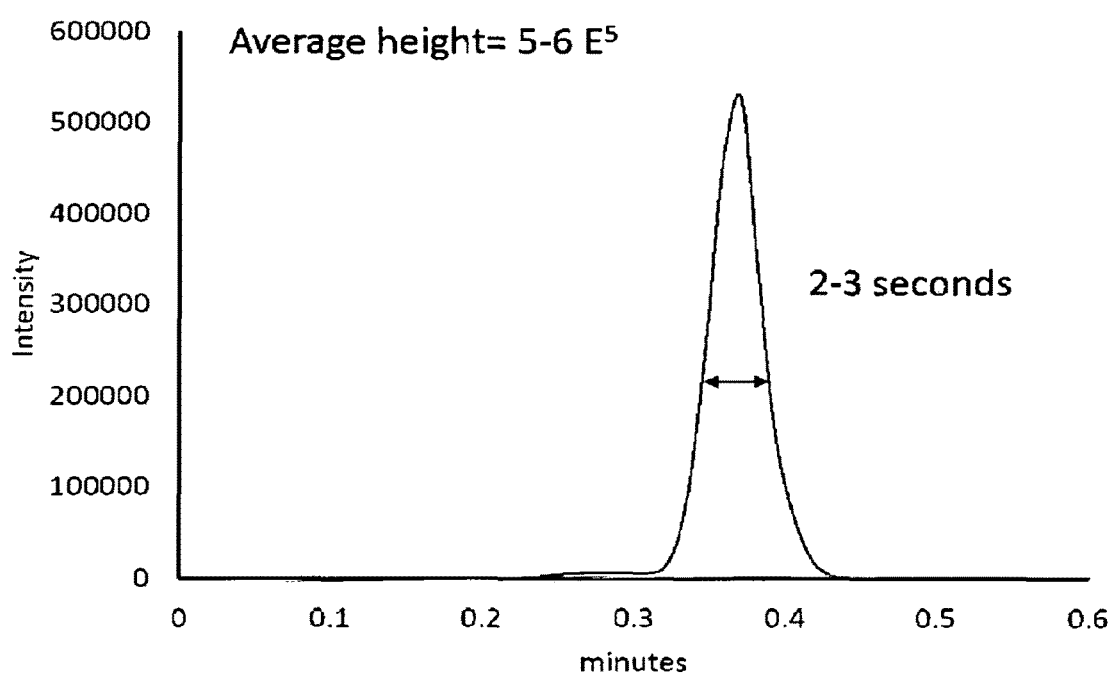
FIG. 7 is an ion chronograph of cocaine extracted and detected using a system and method according to the present disclosure.
Figure 8:
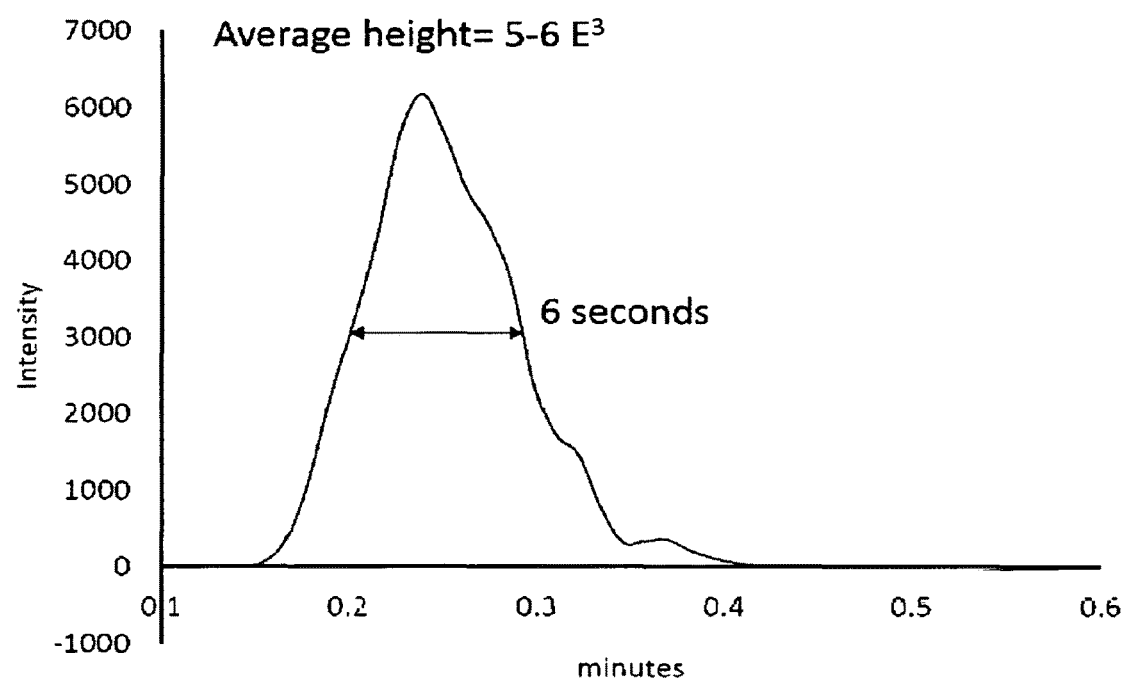
FIG. 8 is an ion chronograph of cocaine extracted and detected using a conventional system and method.

The ion chronograph of cocaine extracted and detected using the method and system described above is shown in FIG. 7, while the ion chronograph of cocaine extracted and detected using a conventional open port probe is shown in FIG. 8. The peak profile in FIG. 7 is very sharp, having a FVVHM of 2-3 seconds. In contrast, the peak profile in FIG. 8 is less sharp, having a FVVHW of 6 seconds. This corresponds to an increase in sensitivity of between 1 and 2 orders of magnitude.

The length of desorption time was evaluated. Desorption times of 5 and 10 seconds were evaluated. The peak heights, standard deviations, and relative standard deviation (% RSD) are shown in Table 2 for four replicate extractions and desorptions. A desorption time of 10 seconds showed better recovered areas, but the improvements were not significant for the tested compounds. Longer desorption times may be used, for example when desorbing a compound with low kinetics of desorption, or when desorbing from an SPME device with a thick coating.

TABLE 2

| | desorption time | | | | | |
|---|---|---|---|---|---|---|
| | 5 s | | | 10 s | | |
| | Peak height | Std. dev. | % RSD | peak height | Std. dev. | % RSD |
| buprenorphine | 6760 | 1527 | 23 | 2520 | 410 | 16 |
| clenbuterol | 551 | 154 | 28 | 641 | 21 | 3 |
| cocaine | 61733 | 14468 | 23 | 196475 | 63640 | 32 |
| codeine | 197500 | 19092 | 10 | 144000 | 31225 | 22 |
| sertraline | 13400 | 2252 | 17 | 23333 | 4994 | 21 |
| fentanyl | 19900 | 2914 | 15 | 37467 | 15205 | 41 |
| oxycodone | 85050 | 20577 | 24 | 39660 | 6437 | 16 |

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

Figure 9:
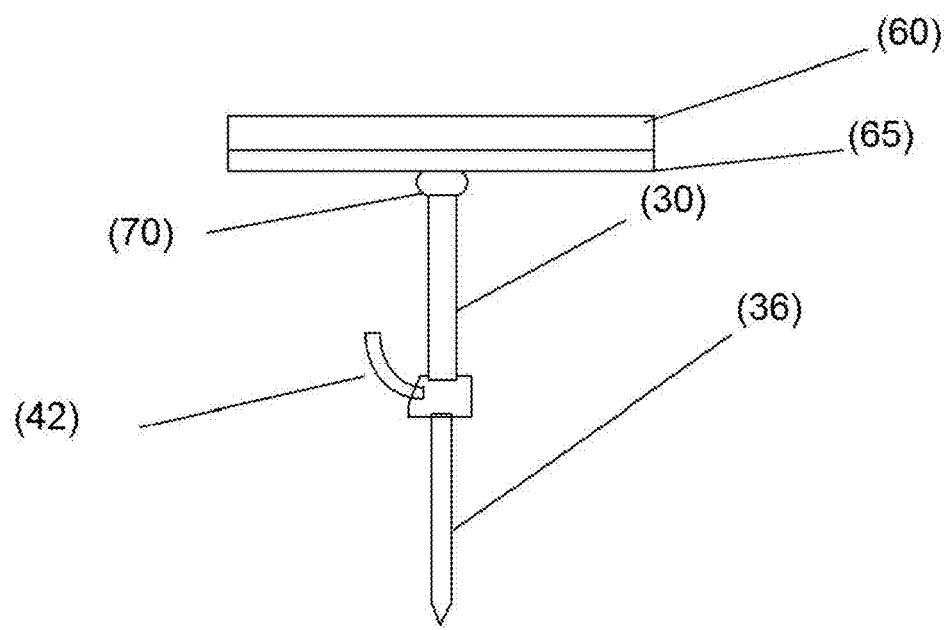
FIG. 9 is an illustration of an exemplary desorption chamber and fluid-isolating flow connector including external SPME device according to the present disclosure.

This application is disclosing the device and method where the microextraction device is a surface with which the solvent contained in the chamber can make contact with. The process is similar to the process described above with a difference that the SPME device consisting of support (60) and coating (65) is located outside the desorption chamber (30) (FIG. 9). In the first step the desorption chamber (30) is filled with the desorption solvent to form a dome (70) which makes a contact with the SPME coating for predetermined time to facilitate extraction of analytes from the coating. The extracted analytes accumulate in the desorption chamber. At the predetermined time the solvent with desorbed analytes is flushed from the desorption chamber through the electrospray to MS in the process described above. This approach allows desorption of large amounts of analytes as the solvent can make contact with large surface area by moving the solvent contact spot (solvent dome) through the whole solid phase microextaction surface. This allows accumulation of large amount of the desorbed analytes in the solvent contained in the desorption chamber isolated from the electrospray flow, resulting in high sensitivity of determination of that analyte, when the solvent is flushed to the mass spectrometer through the electrospray. In addition to uniform distribution of analytes on the surface of the SPME device, the analytes can be distributed in spots (by spotting the sample onto the surface, so multiplexing is possible facilitating quantification of analytes in large number of spots originating from different samples. The support (60) can also be a magnet with magnetic SPME particles collected on it forming a coating (65). Finally, instead of the SPME surface a tissue (in-vivo or ex-vivo) can be exposed to solvent dome resulting in high sensitivity determination and imaging as the device can be in contact with the tissue at a particular place for long periods of time resulting in large accumulation of analytes. The contact with tissue can be direct or indirect via selective permeation membrane in order to simplify the mixture of analytes being concentrated in the solvent. The fluid flows to and from the chamber can be regulated not only by using the pump delivering the solvent (fluid source) and the nebulizer gas flow (fluid injector), but the flows can also be directed by using electrical potential through electroosmotic principle.

EXAMPLE

Setup Description

Figure 10:
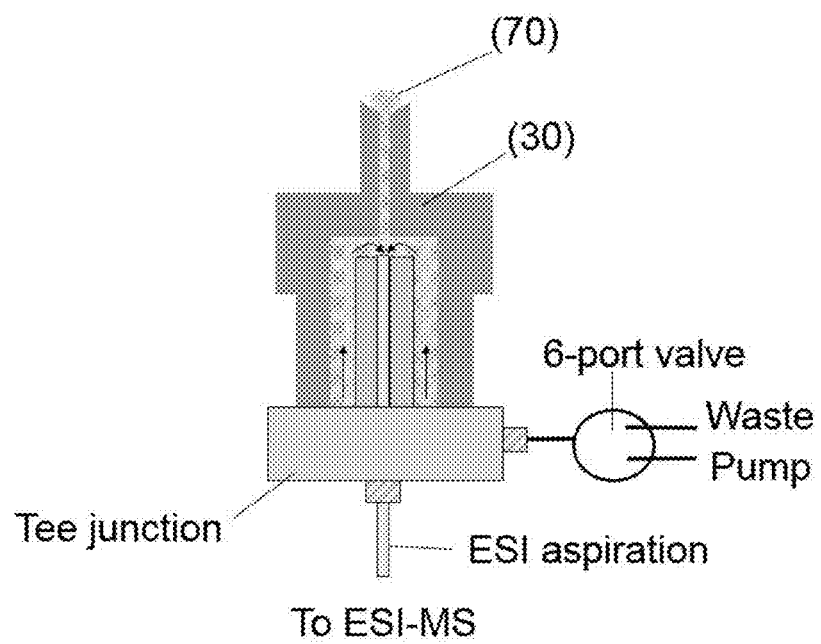
FIG. 10 is a view of an exemplary dome chamber and fluid-isolating flow connector according to the present disclosure.
Figure 11:
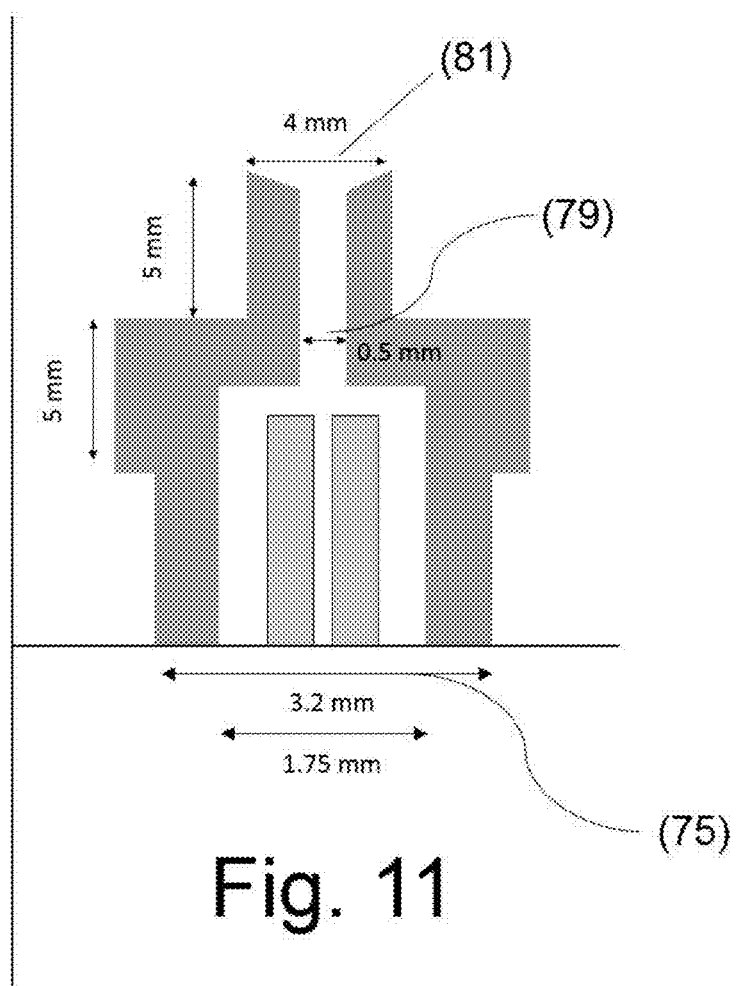
FIG. 11 is a scheme with the dimensions of the dome chamber and fluid-isolating flow connector.

The invention consists in two main sections. As shown in FIG. 10 and FIG. 11, the top piece has a lower hole (75) of 3.2 mm of diameter connected to the upper part by a channel of 0.5 mm and a length of 2 mm (79). The tip of the dispositive has a taper end aiming to reduce the device wetting surface when the droplet is in contact with the sample and avoid potential carry-over between samples. The last 10 mm of the device have a diameter of 4 mm to also minimize the spread of the droplet by capillarity when it is in contact to the flat surface of the sample (81).

The connection between the top piece and the ESI source was described above. Essentially, it comprises two concentric tubes where solvent is provided through a tee junction and fills up the gap formed between these two tubes. Once the solvent reaches the top of the interface, it is aspirated by the inner tube towards the mass spectrometer through the aspiration by Venturi effect generated at the ESI source (38). The outer tube is a 304 stainless steel, 1.75 mm i.d.×3.18 mm o.d.×~5 cm long (McMaster-Carr, Chicago, Ill., USA) and the inner tube is a peek tube; 180 µm i.d.×0.75 mm o.d.×~20 cm long (Idex, Oak Harbor, Wash., USA) embedded inside of a 0.75 mm i.d.×1.52 mm o.d.×15 cm long FEP tubing (Cole-Parmer, Vernon Hills, Ill., USA). The solvent is delivered by a LC pump (200 Series; Perkin Elmer, Santa Clara, Calif., USA) and the ESI and aspiration is generated using Turbolon spray source (Sciex, Concorde, ON, Canada). To increase the aspiration rate, the ESI commercial electrode was substituted with a 150 µm i.d. electrode (McMaster-Carr, Chicago, Ill., USA). The fluidic system was connected by means of a PEEK Tee junction (Idex, Oak Harbor, Wash., USA). As FIG. 1 also shows, the pumping solvent was bypassed with a valve (6-port valve) to rapidly switch the pump flow and permit the suction of the isolated droplet towards the MS.

The operational conditions for the desorption step are: pump flow of 100 µL/min, positive ion mode, nitrogen gases set at GS1=90, GS2=70; curtain gas=25; heated nebulizer temperature=300° C.; and electrospray voltage=5500 V.

Figure 12:
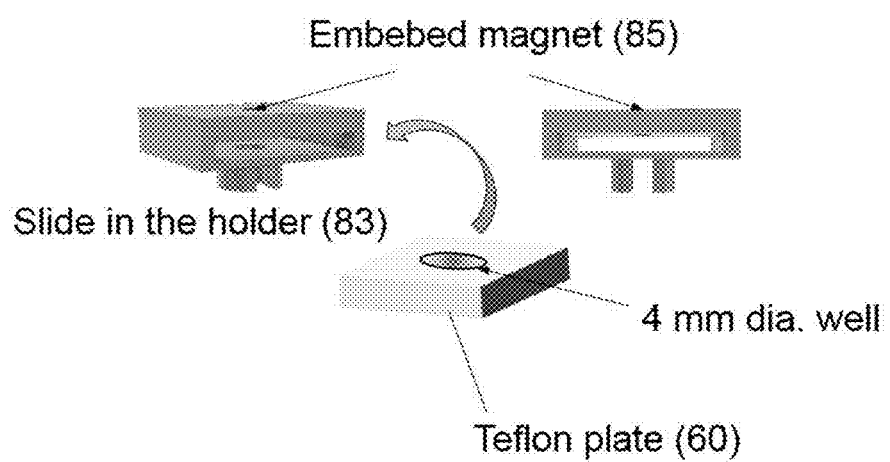
FIG. 12 are the illustrations of the well holder as well as the well where the magnetic particles are contained.

Regarding the second section of the device, FIG. 12 shows the upper holder (83) that allows the physical contact between the droplet and the magnetic particles. Also, the upper part of the holder has a 5 mm diameter×5 mm long embedded rare-earth magnet (85) (Lee-Valley, ON, Canada) which is in contact with the plate keeping the particles attached to its surface. The holder was 3D printed with Nylon and sits perfectly on the top of the invention. The plates are 5 mm thickness Teflon squares of 2 cm×2 cm including a well of 4 mm diameter and 2 mm deep. Once the extraction is performed, the plate is easily slide in the holder.

Figure 13:
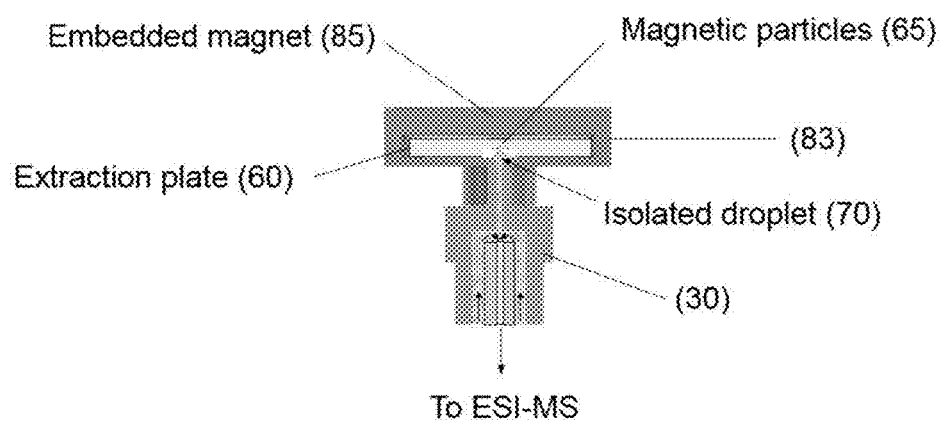
FIG. 13 is a scheme of how the holder containing the well with the nanoparticles is attached to the desorption chamber and fluid-isolating flow connector for desorption of compounds of interest.

In FIG. 13 is observed how the holder containing the well can be positioned on the top of the device for making a precise contact between the isolated droplet and the magnetic particles.

Figure 14:
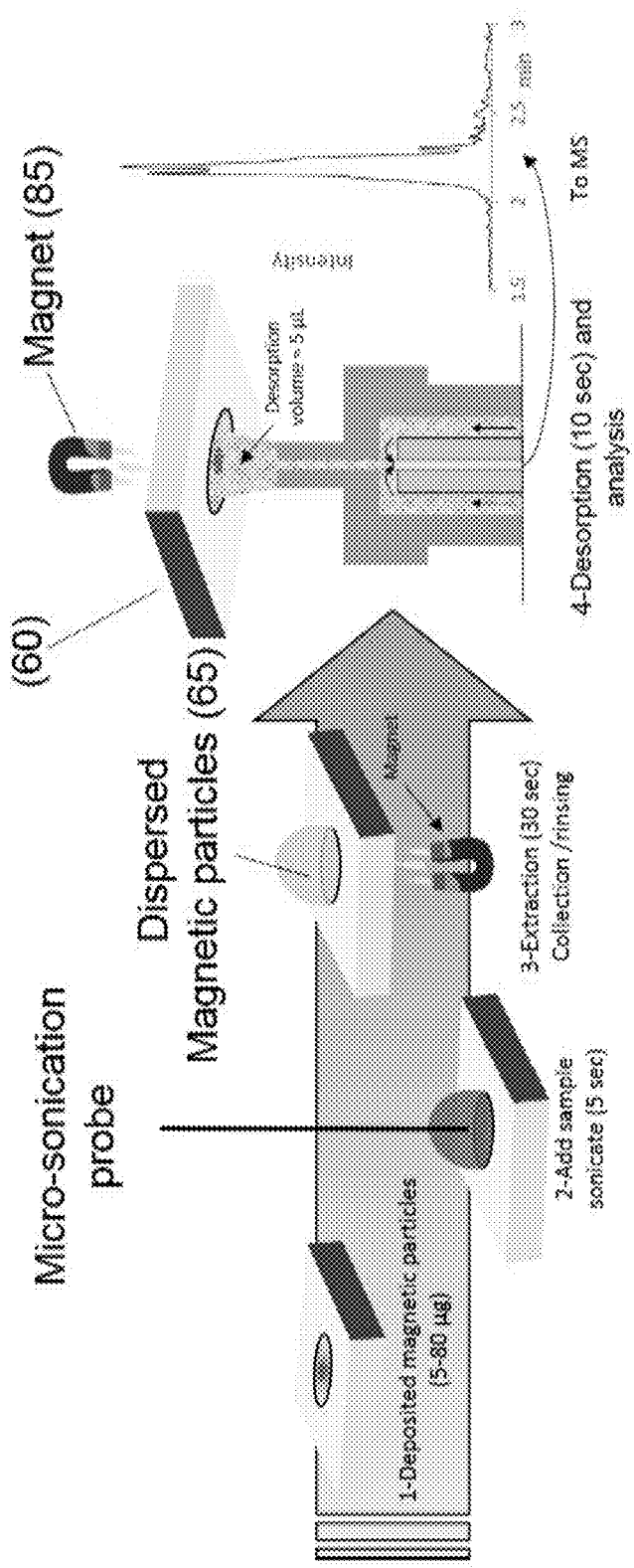
FIG. 14 is a scheme of the analytical workflow to perform extractions from droplets and analyze it using the desorption chamber.

As shown in FIG. 14 the general analytical workflow comprises the dispersion of the magnetic particles (15-100 µg/sample) in a droplet of sample (5 s) allowing extraction for 30 s.

The dispersion is performed adapting a sonication probe by attaching a stainless-steel wire of 250 µm of diameter in order to transfer the ultrasound through this material. Hence, the wire is placed inside the droplet to promote the dispersion of the particles inside the droplet. Because of the size of the particles, they will remain dispersed for times as long as 2 hours, being the determining factor the evaporation rate.

When extraction is finished, a magnetic field is applied for particles collection. Then, a gentle rinsing is done in the presence of the magnetic field. Finally, the isolated droplet of the MOI is put in contact with the collected spot of particles in order to desorb the targeted analytes (10 sec) and quickly transfer them to the MS via ESI ionization.

The solvents employed to operate this embodiment of the invention need to be adequate to desorb the compound of interest. This comprises aqueous/organic mixtures such as methanol, acetonitrile, isopropanol, chloroform, tetrahydrofuran, dimethyl sulfoxide, etc. Also, these solvents can be used with additives to improve the desorption or ionization process such as formic acid, acetic acid, ammonium formate, ammonium acetate and, ammonium hydroxide; metal additives such as copper, iron or any other metal salt capable to form adducts with the analyte of interest; complexing agents such as ethylenediaminetetraacetic acid (EDTA), citrate salts or any other compound capable to produce complexes with the analyte of interest.

To reduce dwell time associated with time required for desorption the desorption solvent can be introduced in advance to placing the SPME device in the desorption chamber. This allows at least for partial desorption to occur prior placing the device in the desorption chamber, so the time for introduction of the desorption solution to the detection device is reduced. The time between advance introduction of the desorption solution and the placement in the desorption device should be optimized to maximize sensitivity of the measurement.

EXAMPLE

Determination of Prohibited Substances

Formic acid (FA), ammonium acetate (both LC-MS grade), and polyacrylonitrile (PAN) were purchased from Sigma-Aldrich (Oakville, ON, Canada). Methanol (MeOH) and water were LC-MS grade and purchased from Fisher Scientific. Cocaine, cocaine d3, fentanyl, fentanyl d5, methadone, methadone d3, propranolol, propranolol d7, sertraline and sertraline d3 were acquired from Cerilliant Corporation (Round Rock, Tex., USA).

PBS and urine samples were spiked with concentrations of cocaine, fentanyl, methadone, propranolol and sertraline ranging between 0.1 and 1000 ng/mL. All employed internal standards (see Table 3) were spiked at 10 ng/mL. The samples were agitated and store for three hours for equilibration.

TABLE 3

Compound and internal standard Log P, minimum required performance limits (MRPL), MRM transitions and MS parameters such as declustering potential (DP), entrance potential (EP), collision energy (CE) and exit potential (CXP).

| Compound | Log P | MRPL (ng · mL$^{-1}$) | Precursor (m/z) | Product (m/z) |
|---|---|---|---|---|
| Propranolol | 3.48 | 100 | 260.070 | 116.111 |
| Propanolol-d$_7$ | | | 267.137 | 116.111 |
| Cocaine | 1.97 | 100 | 304.089 | 182.093 |
| Cocaine-d$_3$ (IS) | | | 307.055 | 185.111 |
| Sertraline | 5.06 | ≤300 | 306.356 | 159.000 |
| Sertraline-d$_3$ (IS) | | | 309.030 | 158.929 |
| Methadone | 3.93 | 50 | 310.048 | 265.007 |
| Methadone-d$_3$ | | | 313.272 | 268.166 |
| Fentanyl | 4.12 | 1 | 337.468 | 188.183 |
| Fentanyl-d$_5$ (IS) | | | 342.261 | 188.111 |

Prior to extraction, an aliquot of 20 µL of a slurry of $Fe_2O_3$—$C_{18}$ nanoparticles 3 mg/mL (60 µg) 50:50 v/v (ether/methanol) was added to the Teflon well. After a few seconds the solvents is evaporated, and the plate is ready for extraction. Then, 40 µL of sample (PBS or urine) was also added to the well. In order to disperse the particles in the droplet a sonication probe was adapted for this aim. Essentially, a stainless-steel wire was attached to the tip of the probe to allow an efficient transference of ultrasound from the probe to the droplet. After dispersion the probe is rinsed with methanol for 5 s to avoid any kind of carry-over. The particles were kept dispersed for 30 s for extraction. The process was finished by applying a magnetic field and, in this way, moving to the bottom of the well all the particles. Once the sample is discarded, the particles were rinsed pouring 400 µL of water onto the particles surface. After that, the well containing the particles is slide inside the holder that will kept the particles fixed to the surface because of the embedded magnet. The dome of the device will touch the surface of the particles and desorb the analytes of interest. After 10 seconds, the valve is switched, and the insulated droplet is drained towards the detector for detection.

Figure 15:
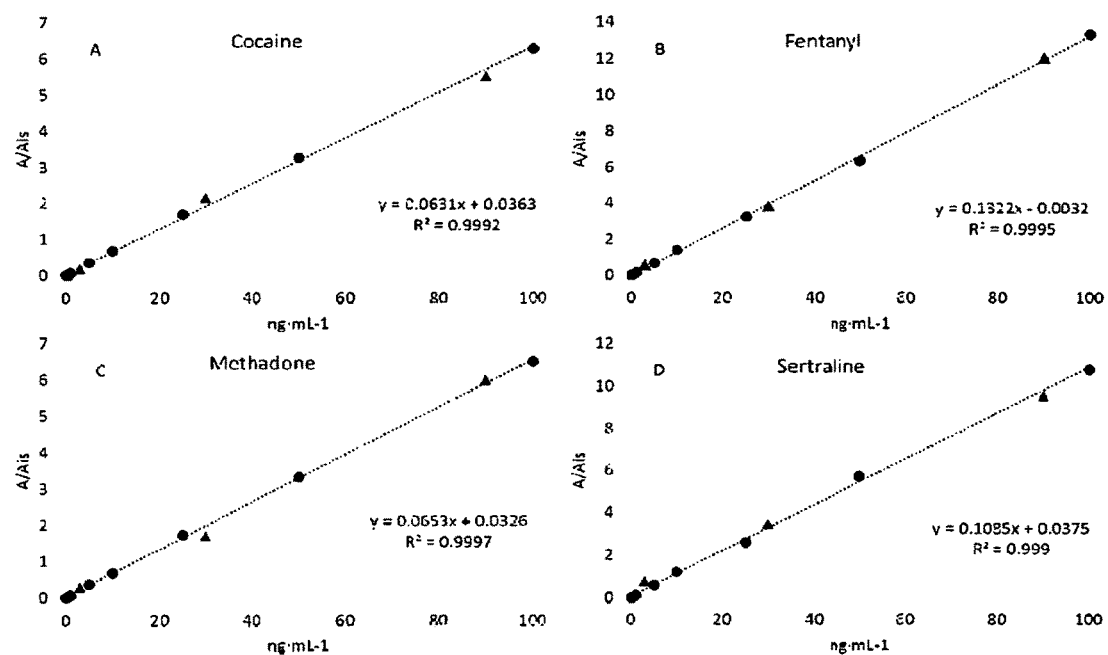
FIG. 15 are graphs illustrating quantitative analysis of PBS spiked with cocaine, fentanyl, methadone and sertraline in a concentration range between 0.5 ng/mL and 100 ng/mL. Cocaine $d_3$, fentanyl $d_5$, methadone $d_3$ and sertraline $d_3$ were added at a concentration of 10 ng/mL as internal standards. The plot is the signal of the analyte divided by the signal of the internal standard against the concentration.

As can be seen in FIG. 15 the calibration curves demonstrating the linearity of the methodology for an extraction of cocaine, fentanyl, methadone and sertraline. Furthermore, it can be also seen the great accuracy of the validation points at 3, 30 and 90 ng/mL and the linearity. In table 4 is showed the limits of quantitation LOQ of the compounds of interest as well as the linear range in PBS. As can be evidenced, the LOQ are ranged between 0.3 and 2 ng/mL for fentanyl and sertraline, and propranolol, respectively.

TABLE 4

Limits of quantitation (LOQ) in ng/mL, linear range for PBS and urine.

|  | PBS | | Urine | |
| --- | --- | --- | --- | --- |
|  | LOQ (ng/mL) | linear range | LOQ (ng/mL) | linear range |
| Cocaine | 1 | 1-100 | 5 | 5-100 |
| Fentanyl | 0.3 | 0.3-100 | 1 | 1-100 |
| Methadone | 0.6 | 0.6-100 | 3 | 3-100 |
| Propranolol | 2 | 2-100 | 5 | 5-100 |
| Sertraline | 0.3 | 0.3-100 | 1 | 1-100 |

Figure 16:
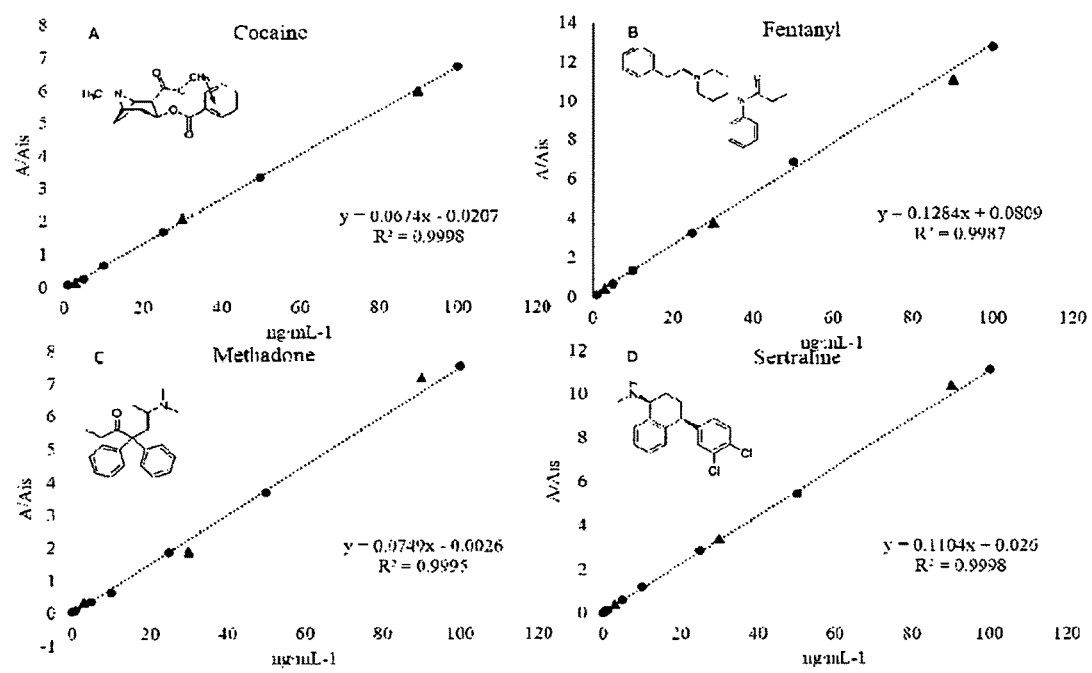
FIG. 16 are graphs illustrating quantitative analysis of urine spiked with cocaine, fentanyl, methadone and sertraline in a concentration range between 0.5 ng/mL and 100 ng/mL. Cocaine $d_3$, fentanyl $d_5$, methadone $d_3$ and sertraline $d_3$ were added at a concentration of 10 ng/mL as internal standards. The plot is the signal of the analyte divided by the signal of the internal standard against the concentration.

In FIG. 16 is shows four representative calibration curves from urine. The linearity values are acceptable as well as the validation points at 3, 30 and 90 ng/mL. In table 4 is also showed the LOQs and linear range for the extraction of cocaine, fentanyl, methadone, propranolol and sertraline. They are in the range between 1 and 5 ng/mL with reproducibility below 15% in all cases.

The invention claimed is:

1. A system for desorbing and detecting an analyte sorbed on magnetic particles working as a SPME device, the system comprising:
   an insulated droplet which acts as a desorption chamber containing the desorption fluid in contact with a device wherein said magnetic particles are collected magnetically,
   a flow injector in fluid connection with the insulated droplet, the insulated droplet and the flow injector being fluidly connected by at least a flow-insulating fluid connector;
   a solvent source in fluid connection with the flow injector; and a fluid switch that:
   (a) in a desorption position, is configured to allow the solvent to be sprayed from the flow injector while the insulated droplet being in contact with the magnetic particles collected in a magnetic holder to allow for analyte desorption from the magnetic particles, and
   (b) in detecting position, is configured to isolate the solvent source from the flow injector by turning off or reducing the solvent flow while maintaining the fluid connection between the flow injector and the insulated droplet so as to transfer desorption solution constituting the insulated droplet through the flow-insulating fluid connector to the flow injector as a substantially undiluted plug of liquid.

2. The system according to claim 1, wherein the SPME device is able to move horizontally in respect to the open to ambient insulated droplet facilitating desorption of analytes from the whole surface resulting in high sensitivity.

3. The system according to claim 1, wherein the insulated droplet is contained within an additional plate containing a well, said plate constructed of polymeric materials including, but not limited to: polybutylene terephthalate (PBT), polytetrafluoroethylene (PTFE), polyethylene (PE) or metals or metal alloys with said well dimensionally configured to be rounded, squared, rhomboidal, pyramidal or conical in shape with a size constraint ranging from 100 µm to 2 cm in diameter, with said plate being secured by an additional holder in a fixed position relative to said insulated droplet and said holder containing an embedded magnet to hold magnetic particles in said well for desorption and prevent said particles from entering said flow injector.

4. The system according to claim 1 wherein the magnetic particles have a magnetic core that has been modified with an extractive phase and has an overall diameter ranging from 2 nanometers to 100 micrometers.

5. The system according to claim 1 wherein 1 to 150 µg of said magnetic particles are used per sample.

6. The system according to claim 4 wherein the extractive phase can consist of but not limited to: $C_3$-$C_{30}$ n-alkanes, hydrophilic-lipophilic balance (HLB) polymers, strong cation exchangers, weak-cation exchangers, strong-anion exchangers, weak-anion exchangers, activated carbon, carbon nanotubes, graphene, fullerenes, silica, zirconia, titanium, antibodies, aptamers, ion metal affinity sorbents, molecularly imprinted polymers, metal oxides, or any other polymer, or combinations of any of these materials.

7. The system according to claim 3 wherein a droplet of liquid can be placed into said well of said plate to be used as a reactor to react with said magnetic particles facilitating extraction, derivatization, digestion, synthesis, decomposition, sequencing or other reactions, or sample preparation on said magnetic particles.

8. The system according to claim 3 wherein an agitation source is incorporated in the device such as but not limited to: vibration, shaking, convection due to temperature gradients, or ultrasonic vibration which is used to disperse said magnetic particles within said well containing a liquid.

9. The system according to claim 1, wherein the detection device is a mass spectrometer, ion mobility spectrometer, or electrochemical or optical spectroscopy-based detector downstream of the flow injector for detecting the desorbed analyte.

10. The system according to claim 1, further comprising a gas source for nebulizing solvent flowing from the flow injector.

11. A method for desorbing and detecting an analyte sorbed on the surface of magnetic particles, the method comprising:
   desorbing at least some of the analyte from the magnetic particles held magnetically in a well and put in contact with an insulated droplet, wherein the desorption solution in the insulated droplet is substantially not flowing to a flow injector;
   flushing substantially all of the insulated droplet to the flow injector as a substantially undiluted plug of liquid towards a detector.

12. The method according to claim 11, wherein the insulated droplet is brought into contact with the magnetic particles with well-defined time in advance of aspiration to the detector.

13. The method according to claim 11, wherein the flow injector is an electrospray needle, a thermospray nebulizer, a microelectrospray needle, an atmospheric pressure chemical ionization nebulizer, an ion-mobility spectrometry nebulizer, an inductively coupled plasma nebulizer, or a system that produces a pressure deferential that drives the solvent flow towards the detection device.

* * * * *